United States Patent
Suovaniemi et al.

(10) Patent No.: US 8,117,928 B2
(45) Date of Patent: Feb. 21, 2012

(54) METHOD FOR SELECTING A PIPETTE TIP AND A DEVICE FOR IMPLEMENTATION

(75) Inventors: Osmo Suovaniemi, Helsinki (FI); Erkki Vesanen, Vantaa (FI)

(73) Assignee: Biohit Oyj, Helsinki (FI)

( * ) Notice: Subject to any disclaimer, the term of this patent is extended or adjusted under 35 U.S.C. 154(b) by 682 days.

(21) Appl. No.: 12/226,596

(22) PCT Filed: Apr. 25, 2007

(86) PCT No.: PCT/FI2007/050226
§ 371 (c)(1),
(2), (4) Date: Oct. 23, 2008

(87) PCT Pub. No.: WO2007/122298
PCT Pub. Date: Nov. 1, 2007

(65) Prior Publication Data
US 2009/0120213 A1  May 14, 2009

(30) Foreign Application Priority Data

Apr. 25, 2006 (FI) .................................. 20060397

(51) Int. Cl.
*G01N 1/14* (2006.01)
(52) U.S. Cl. .................................................. 73/864.16
(58) Field of Classification Search .................. None
See application file for complete search history.

(56) References Cited

U.S. PATENT DOCUMENTS

| 4,529,401 A | 7/1985 | Leslie et al. |
| 5,187,990 A | 2/1993 | Magnussen et al. |
| 5,505,097 A | 4/1996 | Suovaniemi et al. |
| 5,620,661 A | 4/1997 | Sch urbrock et al. |
| 6,090,348 A | 7/2000 | Steele et al. |
| 6,254,832 B1 | 7/2001 | Rainin et al. |
| 6,589,483 B1 * | 7/2003 | Maeda ........................ 422/100 |
| 6,593,146 B1 * | 7/2003 | Lang et al. .................... 436/180 |
| 2005/0125163 A1 | 6/2005 | Suovaniemi et al. |

FOREIGN PATENT DOCUMENTS

| DE | 299 24 175 U1 | 5/2002 |
| EP | 0 155 087 A2 | 2/1985 |
| EP | 0337460 A2 | 10/1989 |
| EP | 0657216 A2 | 6/1995 |
| EP | 1 524 035 A1 | 10/2004 |
| FI | 109337 B | 6/1995 |
| FI | 945786 A | 6/1995 |
| SU | 1677623 A2 | 9/1991 |

OTHER PUBLICATIONS

Russian application No. 2008146405 issued Oct. 1, 2009 with Decision on Grant.

* cited by examiner

*Primary Examiner* — Robert Raevis
(74) *Attorney, Agent, or Firm* — Birch, Stewart, Kolasch & Birch, LLP

(57) ABSTRACT

This invention relates to a method for selecting a plunger-cylinder tip of a pipette and a device for carrying out the method. In the method, the dose size is entered into the control electronics of the pipetting device; the dose size is stored in the control electronics; the amount of doses is entered; and on the basis of the dose size and the amount of doses, the control electronics indicates suitable available interchangeable components on the display.

5 Claims, 1 Drawing Sheet

METHOD FOR SELECTING A PIPETTE TIP AND A DEVICE FOR IMPLEMENTATION

This invention relates to a method for selecting a pipette tip according to the preamble of claim 1 and to a device for the implementation of the method.

Liquid dispensing systems are previously known wherein the functional parameters of an interchangeable component placed in its position for receiving liquid to be dispensed are entered by means of a keyboard for programming the operation of the device. An infusion pump of aforementioned kind has been disclosed e.g. in U.S. Pat. No. 4,529,401. However, said publication does not disclose selecting an interchangeable component.

Manual liquid dispensing in laboratories is usually performed with so-called air displacement pipettes which are easy and economic to use. However, there are situations in which the performance of an air displacement pipette is not sufficient, and in such a case a user selects a pipette to which a disposable piston-cylinder assembly can be connected. Typically, this occurs when using liquids having a high viscosity or high volatility. The pipettes provided with a disposable plunger-cylinder assembly are also especially suitable for so-called multiple dispensing which enables stepwise dispensing of a liquid from a syringe.

In using such interchangeable plunger-cylinder assemblies designed for use in mechanical pipettes, a user places an interchangeable component in its position, sets a parameter typically affecting the dispensing stroke and then checks in a separate table which volume said stroke will give with each type of pipette tip. The laboriousness of the use of such plunger-cylinder assemblies and separate tables will especially accentuate the advantages achievable by the method according to the present invention, such as easy manageability and the precision of dispensing parameters.

Subsequently, pipetting systems have been developed for the aforementioned situations enabling the identification of a mounted interchangeable component. In known pipetting systems, comprising means for identifying different tip types, as disclosed in patent specification FI 109337, also the interchangeable component has to be provided with identifying means whereby, however, when selecting interchangeable components, i.e. tips, the user of the pipetting system must use specially made tips.

U.S. Pat. No. 6,090,348 discloses a pipetting device providing for the use of tips of different sizes, selectable from an electronic menu during use. After the selection, the functional parameters of the program for the pipette are locked in accordance with the volume of the selected tip.

In conventional pipettes, the volumes are thus determined by pipette settings, and the tips of different sizes differ from each other in having tapers of different sizes. When using disposable plunger-cylinder assemblies, the fastening elements for different volumes are of the same size, and therefore, the risk of attaching a wrong plunger-cylinder assembly is very high.

An objective of the invention is thus also to provide a pipetting device wherein the selecting mechanism of an interchangeable component is arranged so that it does not require the use of a specially made tip, but gives a user the possibility to select a tip suitable for a particular pipetting task from a predetermined selection of tips.

This objective may be attained by using an electronic liquid dispenser or a liquid dispenser provided with an electronic control system for performing the method. Preferably, the basic construction of the liquid dispenser may be, for instance, of the same type as pipettes with an electronic tip remover in Biohit's eLINE series.

More precisely, in the method according to the invention, the size of a dose and the amount of said doses are entered in the order of choice; and thereafter the control system indicates an interchangeable component or the interchangeable components available for the relevant dose size and amount of doses. Preferably, the control system primarily indicates an optimal interchangeable component.

According to a preferred embodiment, a plurality of interchangeable component data are first entered (generally prior to the actual use situation), and thereafter those interchangeable components which are not in use are excluded. Prior to use, the size of the dose to be dispensed is input, whereafter the amount of said doses is entered. In a preferred embodiment a broad selection of interchangeable components has been entered to the pipetting device in such a way that the user cannot have any influence thereon, but in advance he/she may deactivate from this selection those interchangeable components which are not available. Therefore, when suggesting interchangeable components suitable for each pipetting task, the control system only takes those interchangeable components, which in fact are available, into consideration.

Preferably, the method according to the invention can be carried out with an apparatus which is an electronically controlled pipetting device, comprising a body having a part for receiving an interchangeable component. The device further comprises electronic control means which control the operation of the pipette, as well as an implementing keyboard and a plunger actuator movable in the direction of the body for dispensing liquid to be pipetted. The device further comprises means for storing data entered into the device, said means preferably being a memory. The data entered to the device includes the dose sizes, the dose amounts as well as information on available interchangeable components. The available interchangeable components are pipette tips comprising a plunger and a cylinder, the measuring volume of which preferably varying between 0.1 and 50 ml.

In a preferred embodiment, the device further comprises electronically controlled locking means, by means of which a detachable interchangeable component may be attached or detached, and means for transferring the state of the locking means to the electronic control means, which preferably is a program. The dosing parameters and/or the type and/or the size of an interchangeable component can be entered into the electronic control means by means of the keyboard of the device.

The pipetting device preferably comprises a locking and detaching mechanism operating under the control system, by means of which the control system can detect the detachment of an interchangeable component.

An advantageous embodiment is also a device, which is an electronically controlled pipetting device (1) comprising a body (2) having a tip portion (3) for receiving a detachable interchangeable component (4); electronic control means for controlling the operation of the pipette (6); means for storing parameters of different interchangeable components formed as a plunger-cylinder unit in the electronic control system (7); an implementing keyboard (8), by means of which the dispensing parameters of an interchangeable component can be input to the electronic control means; a display being connected to the electronic control system (9); a plunger actuator, movable in the direction of the body for dispensing liquid to be pipetted; an electronically controlled locking means adjustable in the pipette in the cross direction of the body for attaching or detaching an interchangeable component; a control means for controlling the movement of the locking means in a direction deviating from the longitudinal direction; and the movement of the plunger actuator can be continued in the longitudinal direction so that the continued longitudinal movement of the actuator may be converted into movement in a direction deviating from the longitudinal direction by means of the control means controlling the movement of the locking means, whereby an interchangeable component is removable preferably axially.

According to the invention, also a pipetting system can be provided, comprising an electronic pipetting device or a pipetting device provided with electronic control, to which pipetting device an interchangeable component is detachably attachable for receiving liquid to be pipetted, the interchangeable component being formed as a plunger-cylinder unit, the plunger of which being movable in the interchangeable component arranged in the pipetting device by means of a plunger actuator of the pipetting device with respect to the cylinder in connection with pipetting movement, for aspiring and discharging liquid to be pipetted, whereby different types of interchangeable components can be arranged in the pipetting device, whereby, however, one and the same relative position of the plunger and the cylinder is arranged for all interchangeable component types so that all interchangeable component types are connectable to the pipetting device in the same manner.

A PRACTICAL EXAMPLE

A pipetting system, comprising a pipetting device provided with electronic control and having a body, and to which pipetting device an interchangeable component is detachably attachable for receiving liquid to be pipetted, said interchangeable component being formed as a plunger-cylinder unit, the plunger of which is movable in the interchangeable component arranged in the pipetting device by means of an plunger actuator of the pipetting device with respect to the cylinder in connection with the movement of the pipetting for aspiring and discharging liquid to be pipetted, whereby several different types of interchangeable components can be arranged in the pipetting device, whereby, however, one and the same relative position of the plunger and the cylinder is arranged for all types.

An electronic pipette may be a hand-held, battery-operated, microprocessor-controlled pipette, comprising a body, which embeds a power supply means for a motor, a controller for controlling the motor, and a means for controlling the operations of the pipette, a display, a tip portion, the plunger of which being arranged reciprocably moveable in the cylinder chamber for changing the volume of the cylinder chamber, and means for converting the rotating movement of the motor into the movement of the plunger in the substantially longitudinal direction of the body of the pipette in the cylinder chamber. The means for controlling the operations of the pipette consist preferably, for instance, of a microprocessor, comprising, in addition to a central processing unit, at least a storage means both for permanent storing of data and/or programs and for temporary storing of data and/or programs as well as a means for connecting the microprocessor to means for controlling the display, to buttons and/or switch keys for controlling the operations, sensors for detecting the status of the controlling elements of the pipette as well as means for transferring the control signals, which is received from the microprocessor, to the controller for controlling the motor. The data and programs stored in the storage means may be stored in the manufacturing stage of the pipette, or a user may store them during use of the pipette.

In a preferred embodiment, in using the pipetting device, a user selects a dispensing mode supporting the function (for instance, the d-mode which is functional in all eLINE Dispenser devices of Biohit and which is used for multiple dispensing). Thereafter the soft-ware requires a user (preferably by means of a message shown on the display) to enter the dose size. When the user has entered the dose size (for instance 10 µl) to the control electronics by means of the keyboard, the software requires the user (preferably by means of a message shown on the display) to input the amount of doses (for instance, 40). When the user has entered the amount of doses to the control electronics, the software suggests (preferably by means of a message shown on the display) a tip suitable for the task in question. The measuring volumes of the tips preferably vary between 1 µl and 50 µl. If there are several alternatives, it is possible to move between these alternatives on the display using the keyboard, and further to select an alternative of choice by means of the keyboard. The keyboard may preferably comprise a roll for facilitating moving on the display.

A user has the possibility to enter in advance the available tip selection to the memory of the pipetting device by means of the same software and keyboard, whereby the software can suggest (preferably by means of a message shown on the display) the available tip size alternatives by excluding those tip types not available for the relevant pipetting task. The pipetting task is determined by the dose size and the amount of doses.

Figure 1:
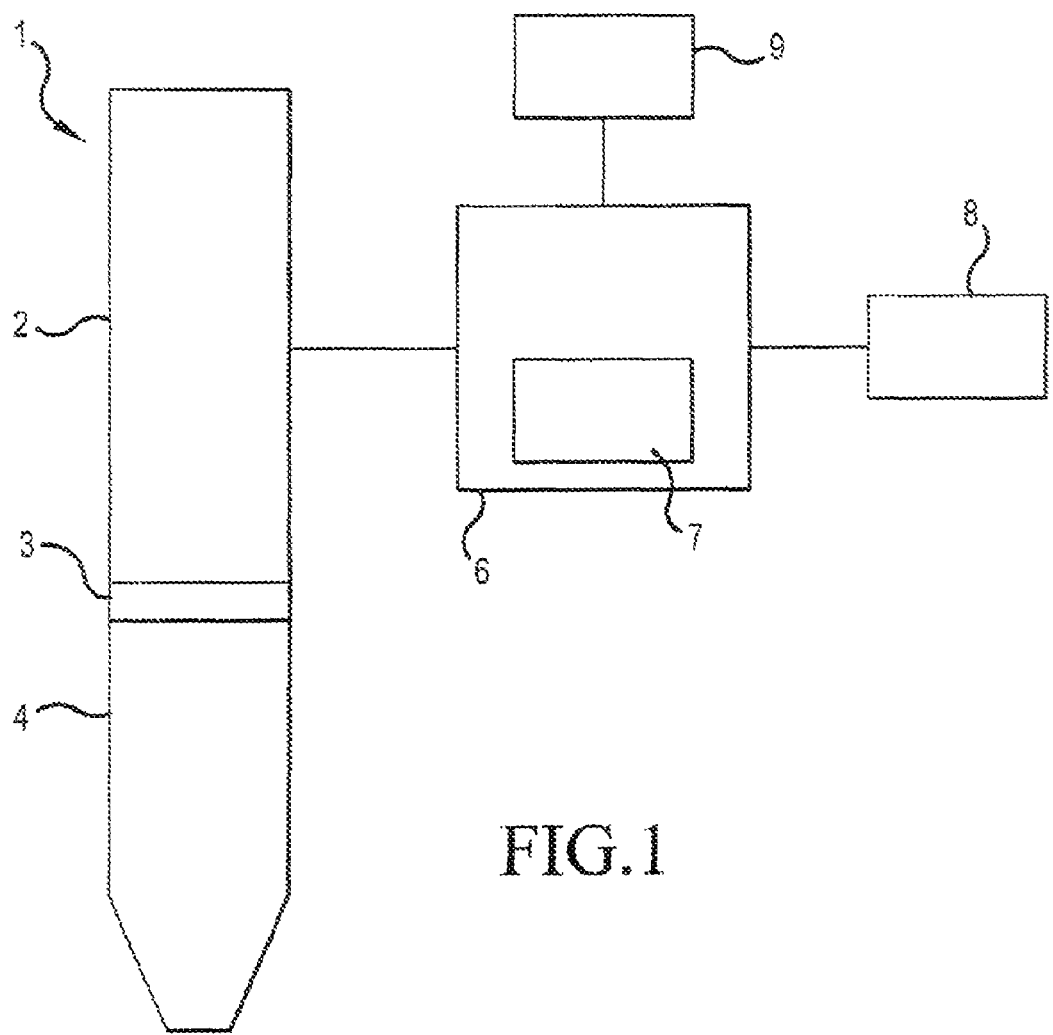
FIG. 1 schematically illustrates an electronically controlled pipetting device of the present invention.

The invention claimed is:

1. A method for selecting an interchangeable component formed as a plunger-cylinder unit to be connected to a pipetting device provided with an electronic control system, the method comprising:
   entering by a user the dose size to the control system of the pipetting device;
   entering by the user the amount of doses to the control system; and
   indicating by the control system, on the basis of the said dose size and the said amount of doses, suitable interchangeable components from a previously stored selection of interchangeable components.

2. The method according to claim 1, wherein part of the stored selection of interchangeable components can be excluded from use.

3. The method according to claim 1, wherein the plunger in an interchangeable component arranged in the pipetting device is moved with respect to the cylinder by means of a plunger actuator, in connection with pipetting movement, for aspiring and discharging liquid to be pipetted, whereby different types of interchangeable components can be provided in the pipetting device, whereby one and the same relative position of the plunger and the cylinder is arranged for all types of interchangeable components.

4. The method according to claim 1, wherein the pipetting device comprises a locking and detaching mechanism operating under the control system, by means of which mechanism the control system can detect the detachment of an interchangeable component.

5. An electronically controlled pipetting device, comprising:
   a body, having a tip portion, to which a detachable interchangeable component is receivable;

an electronic control system which controls the operation of the pipette;
an implementing keyboard;
a plunger movable in the longitudinal direction of the body for dispensing liquid to be pipetted;
a display being connected to the electronic control system; and
means for storing parameters of different interchangeable components formed as a plunger-cylinder unit in the electronic control system, wherein
the dose size and the amount of doses can be entered into the electronic control system by means of the keyboard.

* * * * *